(12) United States Patent
Quaglia

(10) Patent No.: US 12,017,028 B2
(45) Date of Patent: *Jun. 25, 2024

(54) DEVICE FOR APPLYING LIQUID MEDICAL SUBSTANCES

(71) Applicant: NEX MEDICAL ANTISEPTICS S.R.L., Casorezzo (IT)

(72) Inventor: Gianmario Quaglia, Castellanza (IT)

(73) Assignee: NEX MEDICAL ANTISEPTICS S.R.L., Casorezzo (IT)

( * ) Notice: Subject to any disclaimer, the term of this patent is extended or adjusted under 35 U.S.C. 154(b) by 442 days.

This patent is subject to a terminal disclaimer.

(21) Appl. No.: 17/353,132

(22) Filed: Jun. 21, 2021

(65) Prior Publication Data

US 2021/0308438 A1 Oct. 7, 2021

Related U.S. Application Data

(63) Continuation of application No. 16/154,212, filed on Oct. 8, 2018, now Pat. No. 11,071,850, which is a continuation of application No. 14/895,436, filed as application No. PCT/IB2013/058432 on Sep. 10, 2013, now Pat. No. 10,092,737.

(30) Foreign Application Priority Data

Jun. 5, 2013 (IT) .......................... MI2013U000214

(51) Int. Cl.
*A61M 35/00* (2006.01)
*A61M 5/178* (2006.01)

(52) U.S. Cl.
CPC ........ *A61M 35/006* (2013.01); *A61M 5/1782* (2013.01); *A61M 35/003* (2013.01)

(58) Field of Classification Search
CPC ........ A61J 1/2096; A61J 1/201; A61J 1/2089; A61J 1/1406; A61M 35/003; A61M 5/1782; A61M 35/006; A61M 35/00; A61M 5/24
See application file for complete search history.

(56) References Cited

U.S. PATENT DOCUMENTS

| | | |
|---|---|---|
| 4,507,111 A | 3/1985 | Gordon et al. |
| 5,466,465 A | 11/1995 | Royds et al. |
| 6,439,789 B1 | 8/2002 | Ballance et al. |
| 9,610,410 B2 | 4/2017 | Joedicke et al. |
| 2007/0147946 A1 | 6/2007 | Cybulski et al. |
| 2009/0192442 A1 | 7/2009 | Ignon et al. |
| 2014/0114240 A1 | 8/2014 | Joedicke et al. |

FOREIGN PATENT DOCUMENTS

WO 2012116948 A1 9/2012

*Primary Examiner* — Kai H Weng
(74) *Attorney, Agent, or Firm* — Pearne & Gordon LLP; Bryan M. Gallo

(57) ABSTRACT

A device (1) for the application of liquid medical substances (100) comprises a main body (2) extending around a longitudinal axis (X) and comprising a housing portion (3) at a first open end (4) and a delivery portion (5) at a second open end (6) which is opposite the first (4); a hermetically sealed cartridge reservoir (7) containing a liquid medical substance (100); a perforating element (8) disposed inside the main body (2) in a position falling between the housing portion (3) and the delivery portion (5) and such as to achieve the perforation of one end of the cartridge reservoir (7). The perforating element (8) has a tubular shape and comprises, in a central portion thereof, a cylindrical conduit (12) having a cutting edge (14) faced towards the housing portion (3).

5 Claims, 10 Drawing Sheets

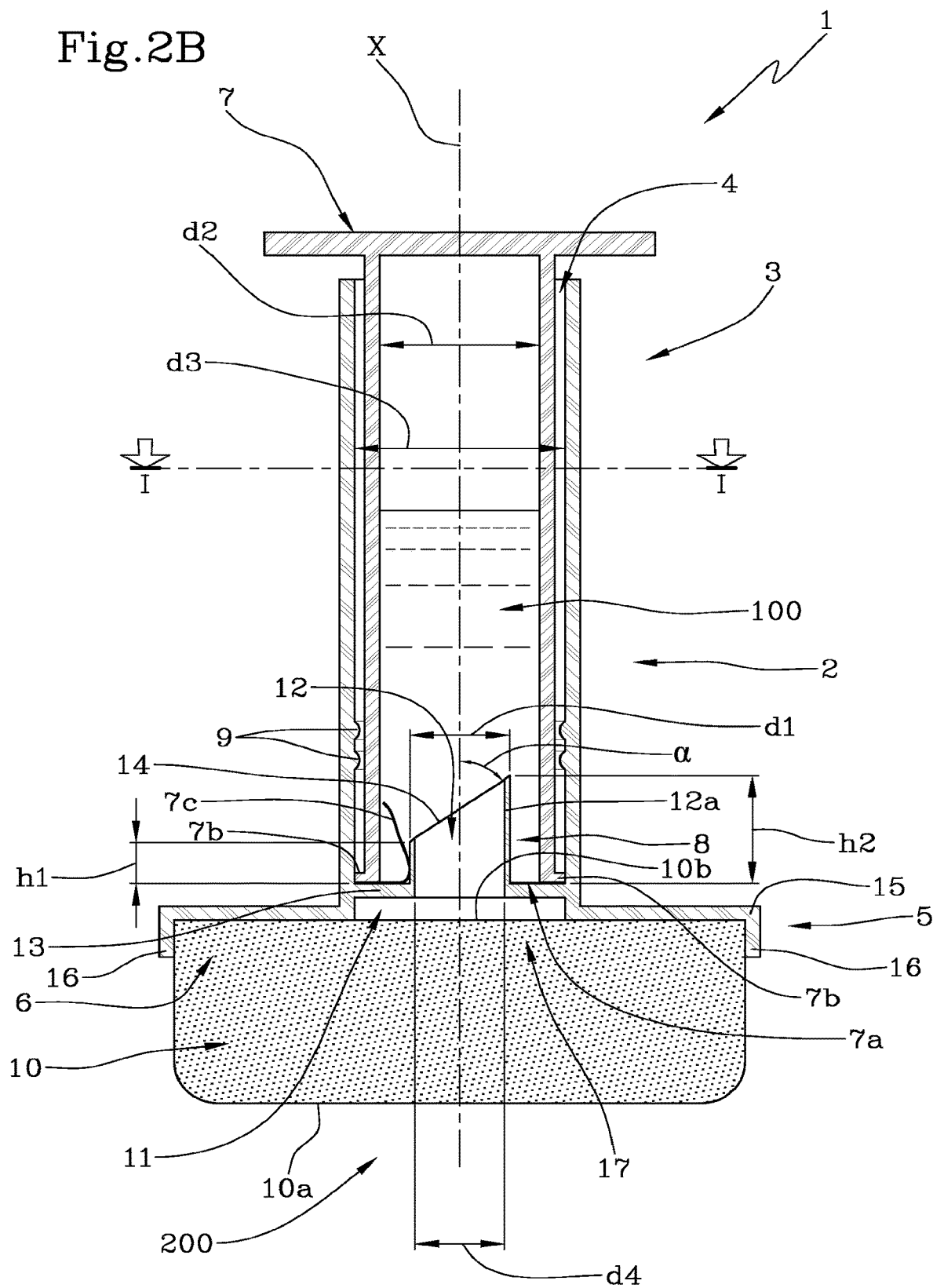

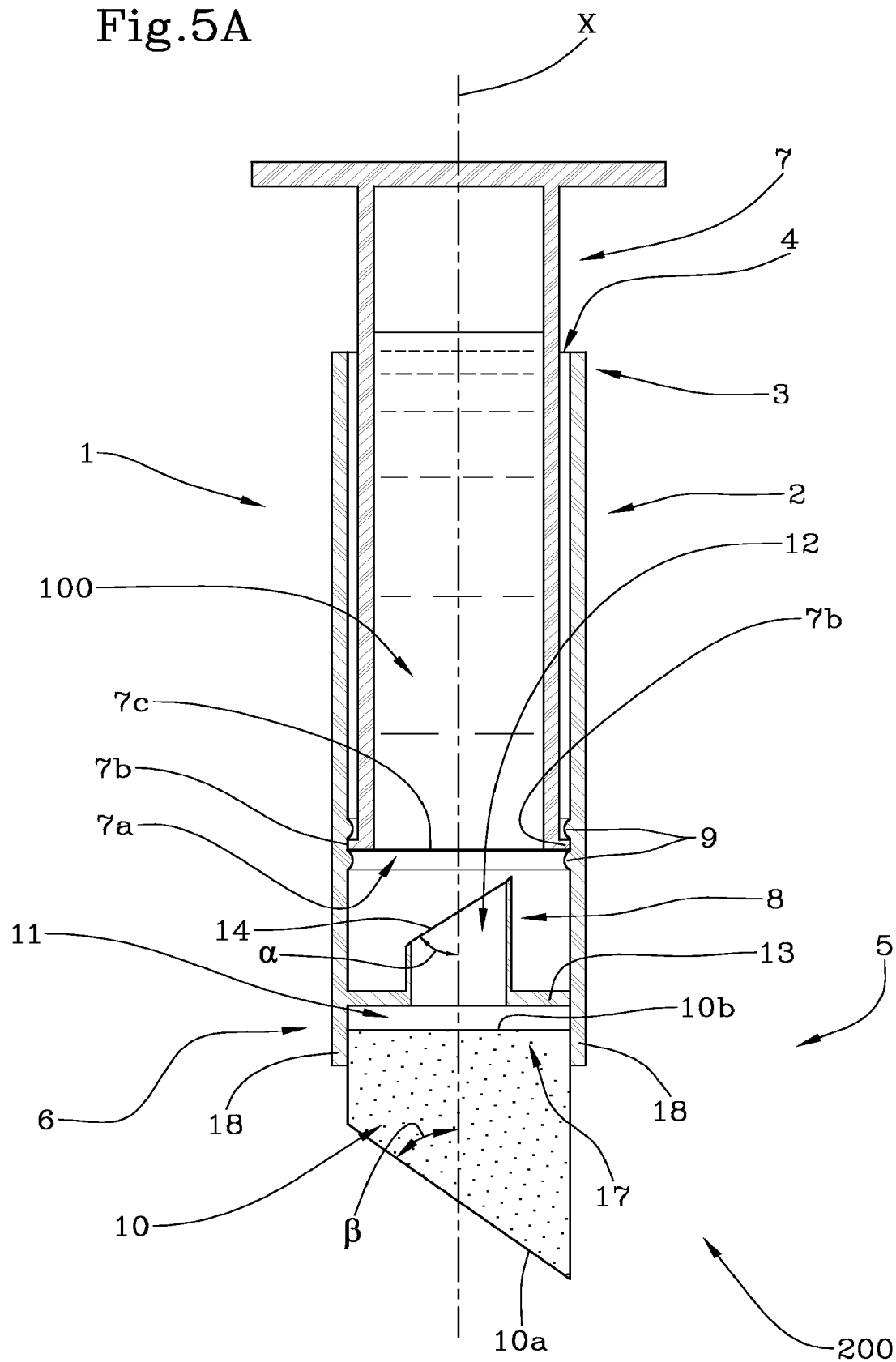

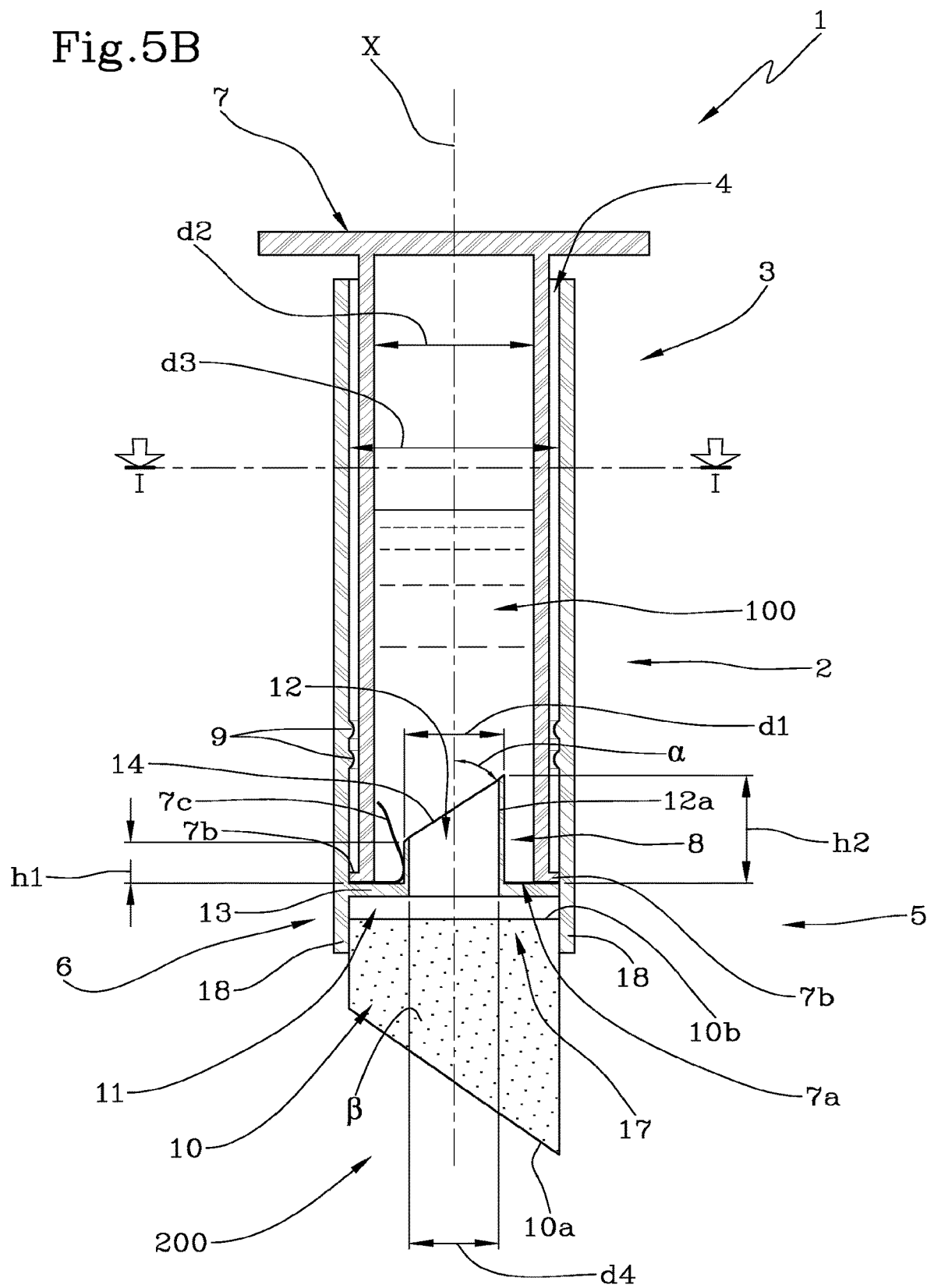

DEVICE FOR APPLYING LIQUID MEDICAL SUBSTANCES

TECHNICAL FIELD

The present invention relates to a device for the application of liquid medical substances.

In particular, the present device has particular application in the realm of medical care, in hospital or health facilities or mobile first aid stations, during situations of emergency or of simple medical care provided by specialized personnel to people who need liquid medical substances to be applied on the skin and in practices related to the preoperative preparation of skin.

In particular, according to the technical field in which the present invention falls, the applicator device mainly delivers liquid medical substances, such as antiseptic and/or disinfectant substances based on chemical components and suitable for treating a person's skin, hence for external use.

Such applicator devices are generally of the disposable type, and thus delivery of the liquid substance is possible only once after the device is activated, until the liquid runs out and/or the pad dries. This is a necessary condition for ensuring the aseptic characteristics of the pad.

PRIOR ART

The device generally includes a main body, preferably extending longitudinally along an axis and housing within it a reservoir containing the medical liquid, sealed by means of a cap. The reservoir can be inserted into the cylindrical body either by sliding it linearly or screwing it around the longitudinal axis.

The cylindrical body generally also defines the handgrip of the device itself for use.

At one end of the cylindrical body, the device has a pad, composed of an absorbent element such as, for example, a natural fabric or spongy elements, for applying the medical substance on the patient's skin.

In an intermediate position between the reservoir and the applicator pad there is a perforating element which serves to tear open the closure cap of the reservoir upon need and permit the discharge of the liquid, which thus impregnates the pad.

The perforating element has a cutting portion capable of breaking the upper wall of the cap; the thickness of the wall depends on the material of the cap and the dimensions concerned, but it must generally enable perforation by means of a simple manual gesture which can also be carried out by a person normally not assigned to use the device. The perforating element is generally placed parallel to the axis of the device, in a coaxial or decentred position relative to the cap of the reservoir itself. Generally, the coaxial position is used when the coupling between the reservoir and perforating element, and hence the activation of the device, is achieved by axially sliding the reservoir into the cylindrical body, whereas the lateral position is used when the coupling between the reservoir and perforating element is achieved by rotating the reservoir around the longitudinal axis of the cylindrical body. In the case of axial coupling, the perforating element includes a central tip, from which cutting profiles extend radially and partially in an axial direction, and is connected to the cylindrical body by means of fastening tabs that support it and keep it in position.

Alternatively, if the coupling is of the rotational type, the perforating element can simply be composed of a pointed spike placed in proximity to an interior wall of the cylindrical body and serving to achieve a progressive tearing along a circular line in the cap of the reservoir during rotation of the latter at the time the device is activated.

With reference to the centrally located perforating element, it occupies the entire internal cross section of the torn cap, so the liquid flows out around the tip in the space remaining between the cutting profiles, alternating with the fastening tabs, and the cylindrical body. This space defines peripheral outflow channels along which the fluid flows.

Based on what is described above, the blade-like portions and radial supporting extensions are angularly distributed around the axis. According to the prior art, the perforating element is made in one piece with the cylindrical body, and thus it has the same characteristics as the material both are made of.

With respect to the method of use of the device, it should be specified that, under normal storage conditions of the device, the reservoir is already partially or entirely inserted into the cylindrical body and held in a provisional locking position typical of the device's storage prior to its activation and actual use.

In particular, the storage position provides for a certain distance between the sealed side of the reservoir and the perforating element designed to open it.

In the prior art, activation takes place as a result of a complete insertion of the reservoir into the main body, which causes the breakage of the reservoir cap by means of the perforating element, thus releasing the medical liquid toward the applicator pad through the aforementioned passage channels.

In the prior art, the main body at the end accommodating the pad has a larger cross section precisely in order to have a greater surface extent of the pad to ensure adequate delivery of the medical liquid.

The known applicator device described above is such as not to be effective under typical operational conditions of use because it shows several disadvantages and nonconformities compared to the correct use in the "clean" practice of the above-described applications.

One may observe, in fact, scant control over the delivery of the medical liquid contained in it, in terms of both quantity and delivery time and in terms of the handling and application of said quantity released on the area to be treated. These disadvantages preclude correct performance of the operating procedures related to the applications described in the present invention.

In other words, the known applicator device has a flow of liquid, during activation, which is not adequately calibrated on the basis of the actual size of the pad, and thus of the skin surface to be treated within a certain time. In particular, irrespective of the pad size, and thus of the skin surface or area to be treated, situations can occur in which the pad is impregnated too little or too much. Such situations can cause risks and problems both for the health personnel and for the patient being treated. Inadequate impregnation can cause an incorrect and/or insufficient application of the medical substance; just as excessive soaking can cause the dispersal of the medical substance outside the skin area to be treated and an application time that is shorter than the minimum necessary based on the characteristics of the medical substance to be applied. In order to favour the outflow of the substance from the reservoir, the known applicator device requires a manual intervention of health personnel, the flow itself being hindered by the perforating element and/or residues of the cap. This intervention generally consists in dabbing the device with vertical movements (effect similar to that of a volumetric pump which facilitates the suction of a fluid) on the part of skin to be treated until complete delivery. This practice presents significant negative aspects and risks when it comes to medical applications, since it does not permit the medical substance to be applied under complete asepsis for health personnel. The known applicator device is thus not suitable for use in a professional setting, in particular for preoperative preparation of the skin, or in first aid situations, since availability and speed of delivery represent essential requirements, together with use under complete asepsis for health personnel.

Furthermore, the known applicator device is such as to provoke, immediately after its activation by health personnel, involuntary and counterproductive outward dispersions of the medical liquid.

These negative factors are mainly ascribable to the perforation and delivery system provided for during activation of the device.

In fact, the tip part designed to open the reservoir tears open the upper wall of the cap in a not very effective manner, such as not to permit an adequate flow to be delivered and the flow is moreover irregular and uneven. The unsuitable configuration of the perforating element obstructs the outflow from the reservoir, said element being positioned right at the centre of the opening made by it, as well as diverting part of the flow of liquid into a peripheral zone non directly facing the pad. The torn parts of the cap lying in the internal part of the container continue to rest on the perforating element and constitute a further element of obstruction to the smooth passage of the liquid.

Moreover, the play necessarily provided for between the diameter of the reservoir and the inner diameter of the cylindrical body (to enable the reservoir to be conveniently pushed by hand) can cause involuntary leaks of the liquid into the gap created between the reservoir and the cylindrical body for the following reason.

In fact, when the device is activated, the upper edge of the reservoir, i.e. the one with the torn closure cap, does not arrive completely in contact with the base of the pad due to the presence of the fastening tabs: this creates a space through which the liquid flowing out can leak and then run along the aforesaid gap if the device is repositioned vertically, with the pad turned upward.

The above-described effect is worsened further if the device must be used in an upright position with the pad positioned at the top: in this case, since in a first step the device must be maintained with the pad turned down to facilitate the impregnation thereof, when the device is turned with the pad up, the medical liquid remaining in the gap can leak out, wetting the handgrip of the device, parts of areas not undergoing treatment and health personnel. For this reason, even when not provided for under the first aid protocol, health personnel should wear sterile disposable protective gloves in order to prevent any contagious transmission to and from the skin.

Object of the Invention

In this context, the technical task of the present invention is to provide a device for the application of liquid medical substances which is free of the above-mentioned drawbacks.

In particular, it is an object of the present invention to provide a device for the application of liquid medical substances which makes it possible to obtain, under completely aseptic and safe conditions, a rapid delivery and, simultaneously, an outflow at a dosage that is calibrated in terms of flow rate (i.e. ml/s), based on the type of medical liquid delivered onto the pad and the use thereof.

It is a further object of the present invention to provide a device for the application of liquid medical substances which makes it possible to achieve an application on skin at a level of quality and safety for the health personnel and the patient that is higher than what is presently possible in the prior art and is above all obtainable under all operational conditions of use of the device itself.

These and other objects are substantially achieved by a device for the application of liquid medical substances according to what is described in one or more of the appended claims.

The dependent claims correspond to further embodiments of a device for the application of liquid medical substances according to the present invention.

Additional features and advantages will be more clearly apparent from the detailed description of a preferred but non-exclusive embodiment of a device for the application of liquid medical substances according to the invention.

BRIEF DESCRIPTION OF THE DRAWINGS

This description is provided with reference to the appended figures, which likewise have purely illustrative purposes and are thus non-limiting, in which:

FIG. 2B is a sectional side view of the device for the application of liquid medical substances illustrated in FIG. 2A;

FIGS. 5a and 5b each represent a sectional side view of the device for the application of liquid medical substances to which the present invention relates, in accordance with a second embodiment, in a non-operational and operational condition, respectively;

DETAILED DESCRIPTION OF PREFERRED EMBODIMENTS OF THE INVENTION

Figure 1A:
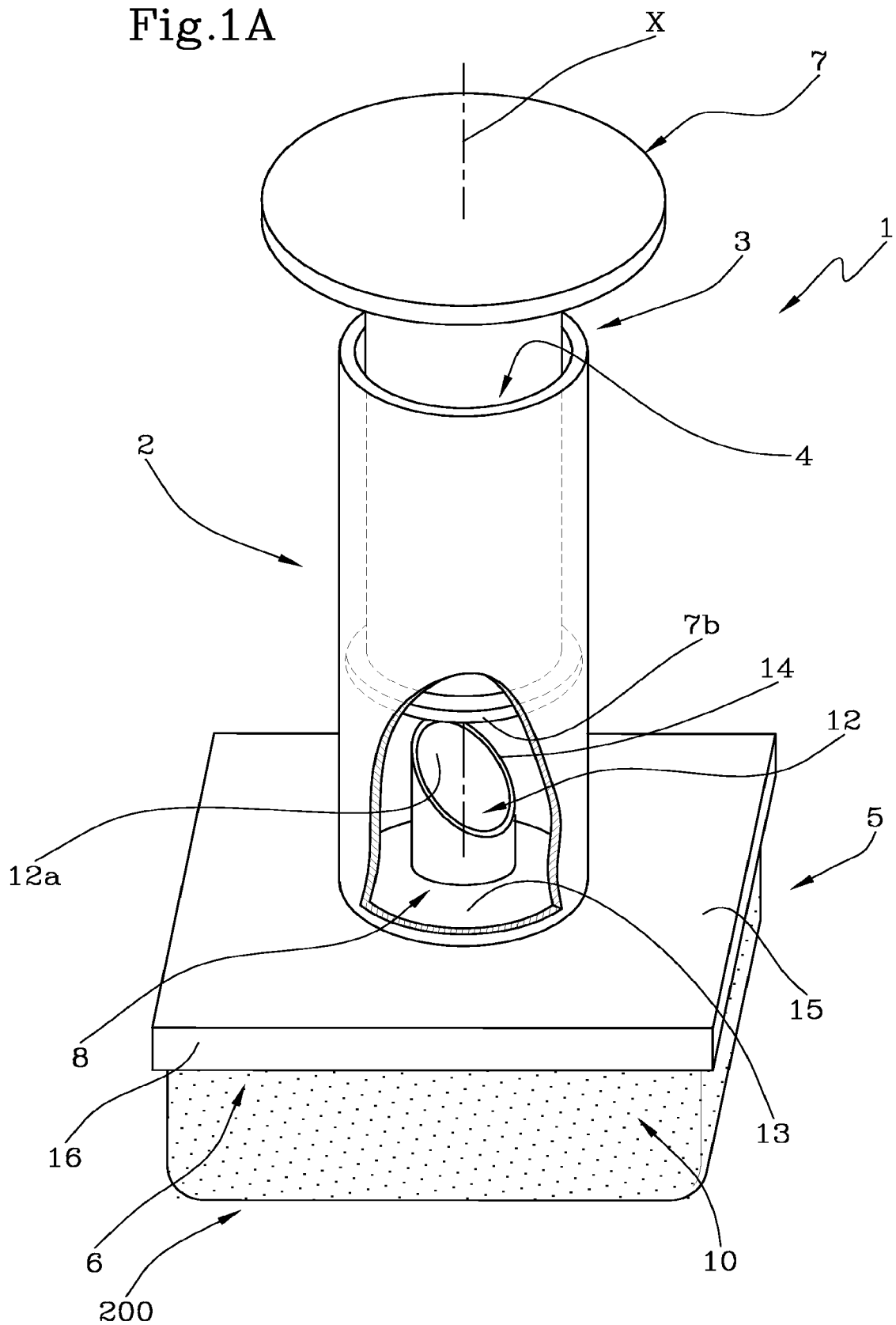
FIG. 1A is a perspective view of a device for the application of liquid medical substances in accordance with the present invention, in an operational condition in which the device is not activated.

With reference to the appended figures, 1 indicates overall a device for the application of a liquid medical substance according to the present invention.

In the preferred embodiment, illustrated in the appended figures, the device 1 comprises a main body 2, which extends around and along a longitudinal axis X, comprising a housing portion 3, at a first open end 4, and a delivery portion 5, at a second open end 6, which is opposite the first.

The device 1 further comprises a hermetically sealed cartridge reservoir 7 containing a liquid medical substance 100, which is at an openable end 7a and adapted for being inserted inside the housing portion 3. The openable end 7a of the reservoir 7 is the one that is completely inserted inside the housing portion 3.

Advantageously, the coupling between the reservoir 7 and housing portion 3 of the main body 2 takes place by sliding along the axis X. However, it is also possible to envisage, according to an unillustrated alternative configuration, a rotational type of coupling, i.e. achieved by screwing the reservoir 7 around the axis X inside the housing portion 3, which, in such a case, will be threaded accordingly.

There is a perforating element 8 disposed inside the main body 2, in a position falling between the housing portion 3 and the delivery portion 5.

The perforating element 8, described in detail further below, is the element used to open the reservoir 7 at the aforesaid sealed openable end 7a. This is achieved by pressing the reservoir 7 inside the housing portion 3 until tearing open the aforesaid sealed openable end 7a as a result of the pressure on the latter by the perforating element 8.

Advantageously, the perforating element 8 has an internally hollow tubular shape and comprises a cylindrical conduit 12 extending away from a flanged annular base 13, adjacent to the delivery portion 5, toward the housing portion 3.

In other words, the perforating element 8 has, at one of its ends, a flanged annular base 13 for connecting it with the main body 2; the perforating element 8 projects from the base 13 toward the housing portion 3 of the reservoir 7.

Preferably, the cylindrical conduit 12 also has a circular or oval cross section, having an outer diameter d1 comprised between 3 and 15 mm, preferably between 5 and 10 mm, even more preferably between 7 and 9 mm. The cylindrical conduit 12 can be coaxial with the axis X or be decentred.

Moreover, the cylindrical conduit 12 has a small wall thickness 12a, preferably comprised between 1-2 mm.

At its free end, opposite the one connected to the base 13, the cylindrical conduit 12 has a cutting edge 14, turned toward the housing portion 3. The conduit 12 serves to place the housing portion 3 in fluid communication with the delivery portion 5, and hence the reservoir 7 in fluid communication with the delivery portion 5 once the device is activated.

The base 13 separates the delivery portion 5 from the housing portion 3. Preferably, the base 13 of the perforating element 8 has the same section as the housing portion 3, and is thus in the shape of a closed circular ring disposed around the cylindrical conduit 12. Furthermore, the annular base 13 is preferably coaxial with the longitudinal axis X and preferably lies in a plane perpendicular to the axis X.

Advantageously, the base 13 is suitable for receiving, in a support relationship, the end 7a of the reservoir 7 which is torn open by the perforating element 8.

Figure 2A:
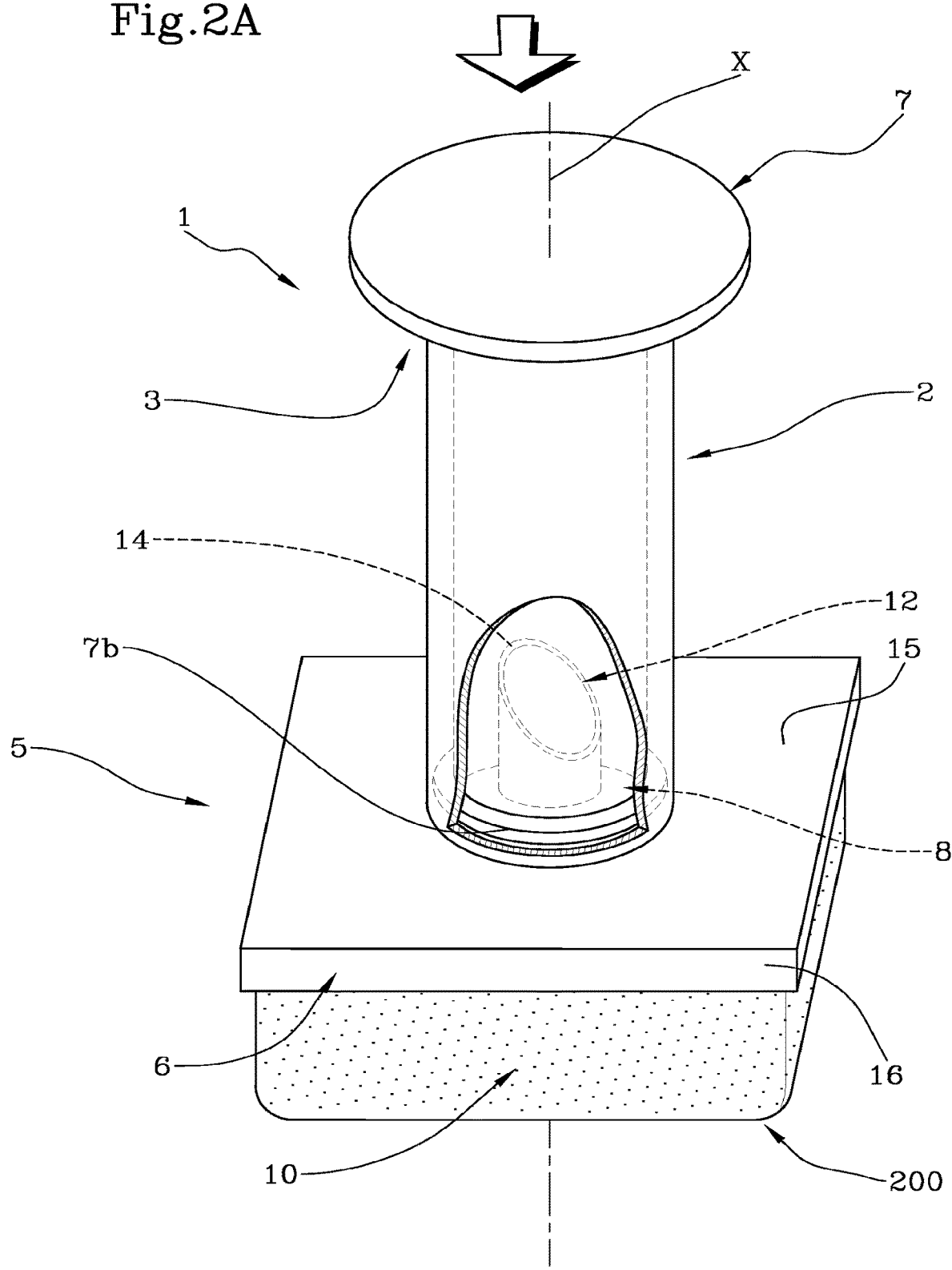
FIG. 2A is a perspective view of a device for the application of liquid medical substances in accordance with the present invention, in an operational condition in which the device is activated.
Figure 3:
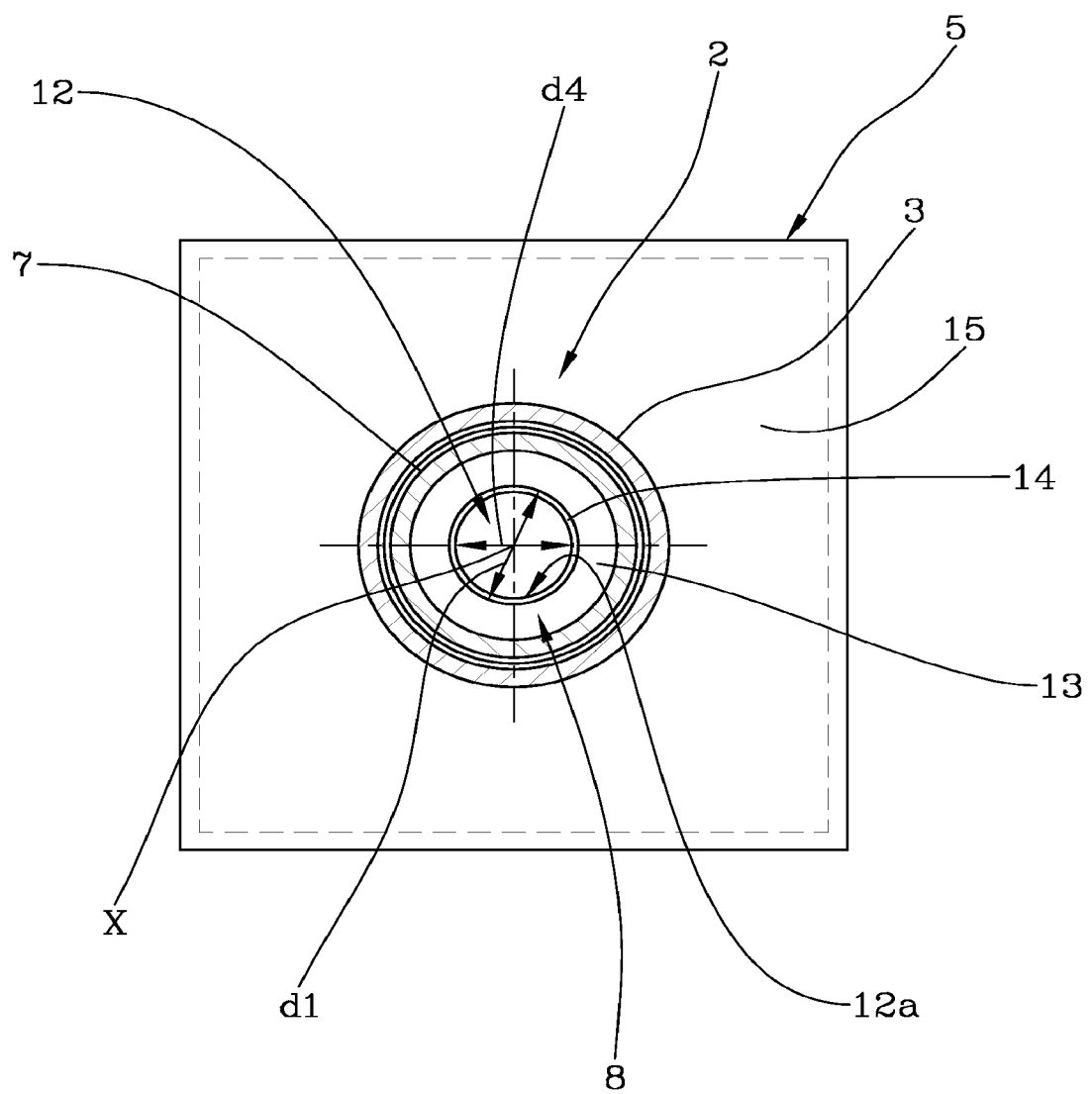
FIG. 3 is a sectional plan view of the device for the application of liquid medical substances, in accordance with the present invention.
Figure 4:
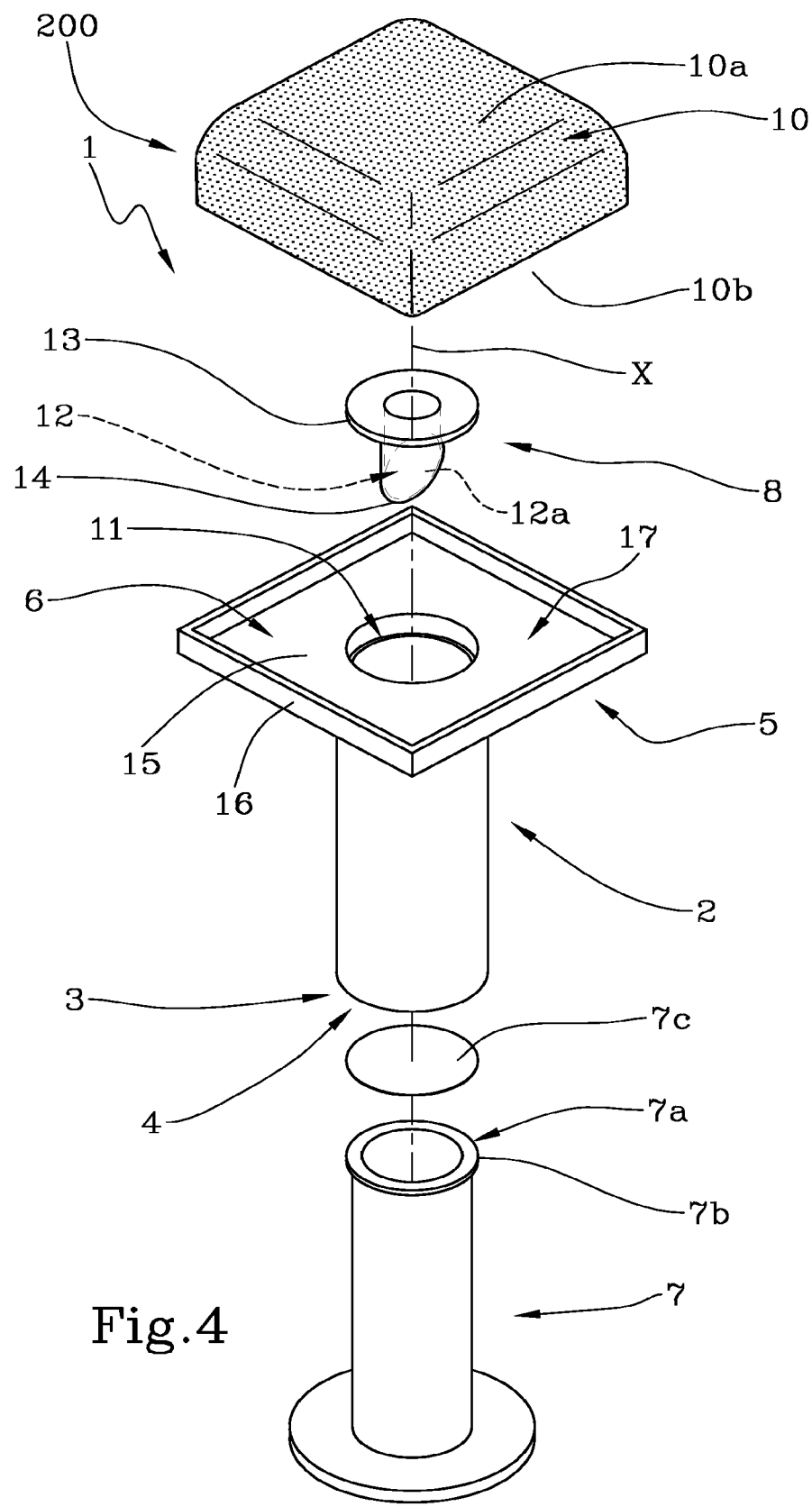
FIG. 4 illustrates an exploded view of the device for the application of liquid medical substances according to the present invention.

Advantageously, the cutting edge 14 of the cylindrical conduit 12 extends along a closed line which delimits, at least partially, the conduit 12. Advantageously, the cutting edge 14 lies in an inclined plane, lending the conduit 12 the shape of a circular cylinder with a slanted cut at the end corresponding to the cutting edge 14 itself, as illustrated in FIGS. 1A and 2A.

Preferably, the inclination of the aforesaid plane in which the cutting edge 14 lies in is comprised between 30° and 60°, preferably equal to an angle α of 45° relative to the longitudinal axis X.

In addition, being one end of the wall 12a of the cylindrical conduit 12, the cutting edge 14 has the same thickness as the wall 12a or, at most, a blade-like tapered profile.

The main body 2 represents a basic element of the device 1, precisely because of its specific geometric and dimensional features, which make it the element in which and on which the device 1 is assembled and completed during a production step.

Preferably, the main body 1 has an axisymmetric shape, in which the housing portion 3 has a curvilinear cross section, preferably circular or elliptical, is hollow on the inside and communicates with the outside 200. The delivery portion 5 can also have an axisymmetric shape with a curvilinear, preferably circular or elliptical, or polygonal cross section.

In an alternative configuration, the reservoir 7 and the main body 2 can also have a cylindrical shape with a polygonal cross section.

The housing portion 3 is designed to contain the cartridge reservoir 7 for nearly the whole length of the housing portion 3 itself.

Preferably, the housing portion 3 also extends longitudinally in such a way as also to ensure, simultaneously with what has been described above, a comfortable, secure grip during use of the device 1.

In particular, the housing portion 3 has an inner diameter d3 that is similar to and just slightly larger than the outer diameter of the cartridge reservoir 7, and hence such as to enable the reservoir 7 to be inserted without any particular interference or friction.

Figure 1B:
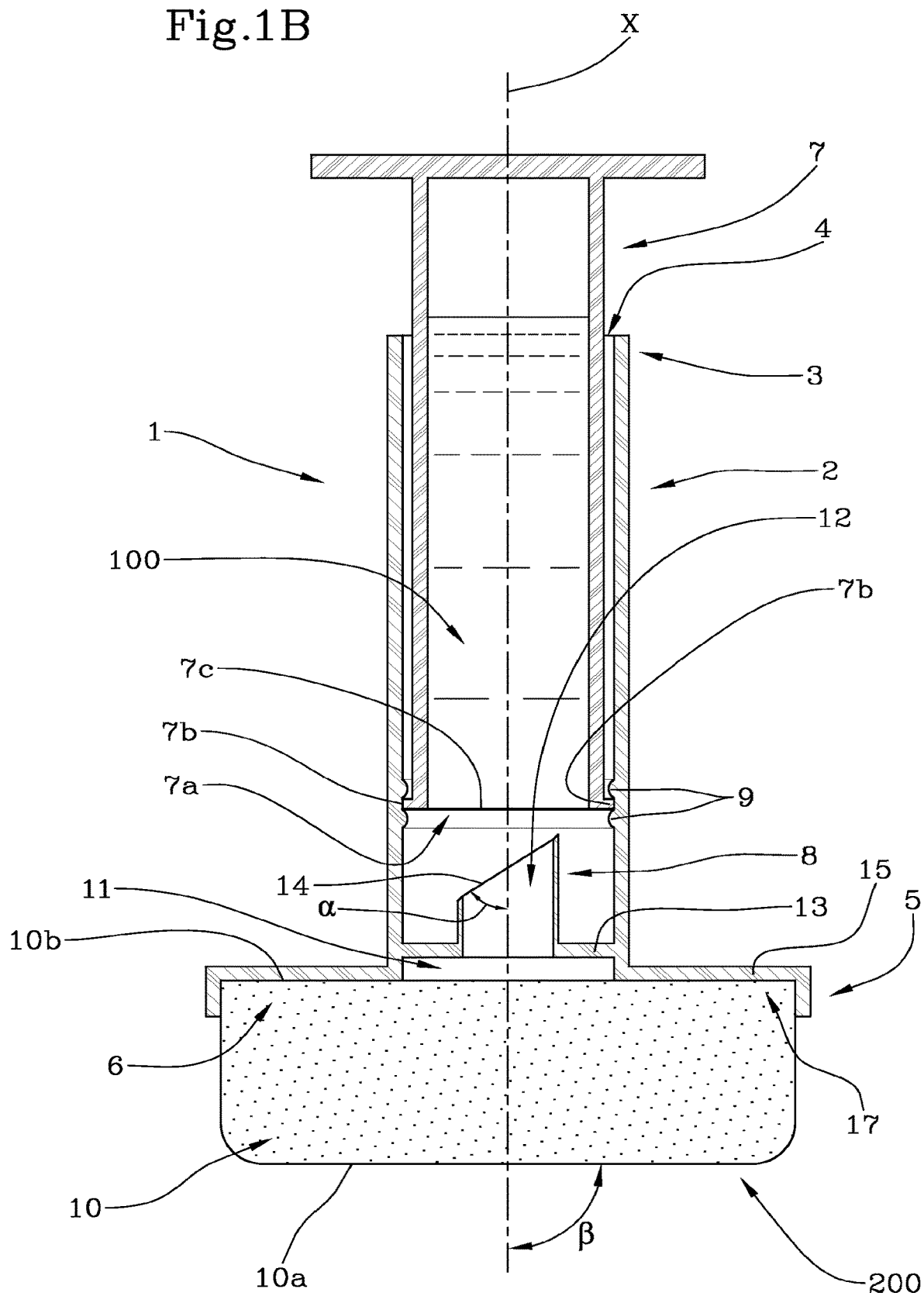
FIG. 1B is a sectional side view of the device for the application of liquid medical substances illustrated in FIG. 1A.

Preferably, the housing portion 3 of the main body 2 has retaining means 9 on the interior walls such as to create a reversible locking with the cartridge reservoir 7. This is an effective solution to enable the reservoir 7 to be held stably in a position of partial extraction from the housing portion 3 (as shown in FIGS. 1A, 1B), suitable for being maintained throughout the duration of storage of the device 1, prior to actual use, in a storage facility or in the compartments that mobile first aid vehicles are fitted with. The retaining means 9 maintain the reservoir 7 in a non-operational position, and hence the device 1 in a non-activated configuration. Preferably, the aforesaid retaining means 9 are formed with one or preferably two annular projections positioned on the interior wall of the housing portion 3, in proximity to the delivery portion 5.

In this manner, the double ring formed by the retaining means 9 prevents both the reservoir 7 from being slipped out of the housing portion 3 involuntarily and the device 1 from being accidentally activated as a result of the reservoir 7 being slid all the way down to the base 13.

In detail, the housing portion 3 extends longitudinally for a length comprised between 50 mm and 200 mm, preferably comprised between 70 and 150 mm.

Advantageously, at the end which is completely inserted inside the housing portion 3, the reservoir 7 has a flange-shaped edge 7b having a radial extent equal to the size of an inner diameter d3 of the housing portion 3.

The shaped edge 7b is reversibly engageable, by pushing, with the aforesaid retaining means 9, which are shaped, as said, like one or more annular projections on the interior surface of the housing portion 3.

The position of partial insertion of the reservoir 7 into the housing portion 3, and hence the non-operational condition of the device 1, is defined by the engagement of the shaped edge 7b with the annular retaining means 9. In such a condition, in fact, the perforating element 8 is disengaged from the reservoir 7.

Once the device is activated, on the other hand, the flange-shaped edge 7b comes up against the base 13 of the perforating element 8.

Other forms of the above-described retaining means 9 are in any case possible, though not illustrated, and fall within the scope of the same functional concept.

To activate the device and thus obtain the perforation of the reservoir by the perforating element 8, manual pressure must be exerted on the reservoir 7; this force causes the disengagement of the shaped edge 7b from the retaining means 9 on the interior wall of the housing portion 3 and thus permits the reservoir to slide further toward the base 13. During this sliding, the openable end 7a of the reservoir 7 meets the perforating element 8, which, following a more intense and prolonged action of pressing, tears open the openable end 7a, placing the reservoir in fluid communication with the delivery portion 5 by means of the cylindrical conduit 12.

The delivery portion 5 represents the interface part of the device 1, through which the medical liquid 100 is applied by means of a pad 10 which is an integral part of the delivery portion 5.

Advantageously, the pad 10 is made of a porous and/or spongy material. In particular, the porous or spongy material is such as to have at least a structure with pockets or internal cavities open toward the outside 200 and communicating with one another, and is suitable for being impregnated with a liquid, such as the medical liquid 100 and, in the case concerned, for releasing it onto a patient's skin.

Preferably, the material the pad 10 is made of can be of a plastic type, made with natural materials or ones obtained by means of specific chemical processes, and it can have a soft consistency, or else be rigid and non-deformable.

In a first embodiment illustrated in FIGS. 1A, 1B, 2A, 2B, 3, 4, 5A and 5B, the pad 10 is housed in a seat 17 of the delivery portion 5 designed to hold it in place by means of gluing or electric welding or else by penetration of a certain number of elements with a pointed shape into the material of the pad 10 so as to provide an interlock.

The housing seat 17 for the pad 10 can be defined by a flanged base 15, preferably projecting from the second open end 6 of the main body 2, and have a circular, rectangular, square or polygonal shape; therefore, the base 15 has a larger diameter or size than the diameter or cross section of the main body 2, as illustrated in FIGS. 1A, 1B, 2A, 2B, 3, 4. Alternatively, as illustrated in FIGS. 5A and 5B, the seat 17 can be defined by an extension 18 of the side walls of the main body 2 beyond the base 13 (FIGS. 5A and 5B).

In the first case, the housing seat 17 for the pad 10 is defined by the flanged base 15, which may be endowed with a perimeter shoulder 16, and by the base 13 (FIGS. 1A, 1B, 2A, 2B, 3, 4), and in the second case it is defined again by the base 13 and the extension 18 of the side walls of the housing portion 3 (FIGS. 5A, 5B).

In accordance with these two configurations, the pad 10 is advantageously cylindrical in shape and has the same section area as the delivery portion 5 with which it is stably associated and, in particular, the seat 17: therefore, the pad 10 has a circular, rectangular, square or polygonal cross section, with base surfaces 10a and 10b which are preferably flat and parallel to each other, as shown in FIGS. 1A, 16, 2A, 2B, 3, 4, or inclined, as can be seen in FIGS. 5A and 5B.

Though not expressly illustrated, the device according to the first configuration (shown in FIGS. 1A, 1B, 2A, 2B, 3, 4) can also have associated with it a pad having the base surfaces 10a and 10b inclined relative to each other and, vice versa, the device in accordance with the second configuration (illustrated in FIGS. 5A and 5B) can have associated with it a pad having the base surfaces 10a and 10b parallel to each other.

Another unillustrated embodiment envisages the flanged base 15 which is inclined relative to the axis X so as to orient the pad with the base surfaces 10a and 10b in an inclined position relative to the same axis X. Having the base surface 10a exposed to the outside environment 200 in an inclined position relative to the device's axis of extension X can facilitate its use and ease of handling, given that this is the surface which is mostly in contact with the skin.

Based on what was previously affirmed, therefore, the device 1 advantageously envisages the orientation of the pad 10 in the delivery portion 5 according to different embodiments, not completely illustrated in the appended figures. In particular, the pad 10 can take on a flat configuration of the base surfaces 10a, 10b with an angle β relative to the longitudinal axis X comprised between 90° and 30°. In the embodiment illustrated in the appended FIGS. 1A, 16, 2A, 2B, 3, 4 the angle is 90°, i.e. the base surfaces 10a and 10b are both orthogonal to the axis X.

In the embodiment illustrated in FIGS. 5A and 5B, only the upper base surface 10a is inclined relative to the axis X, whereas the base surface 10b is orthogonal to the axis X.

Figure 6A:
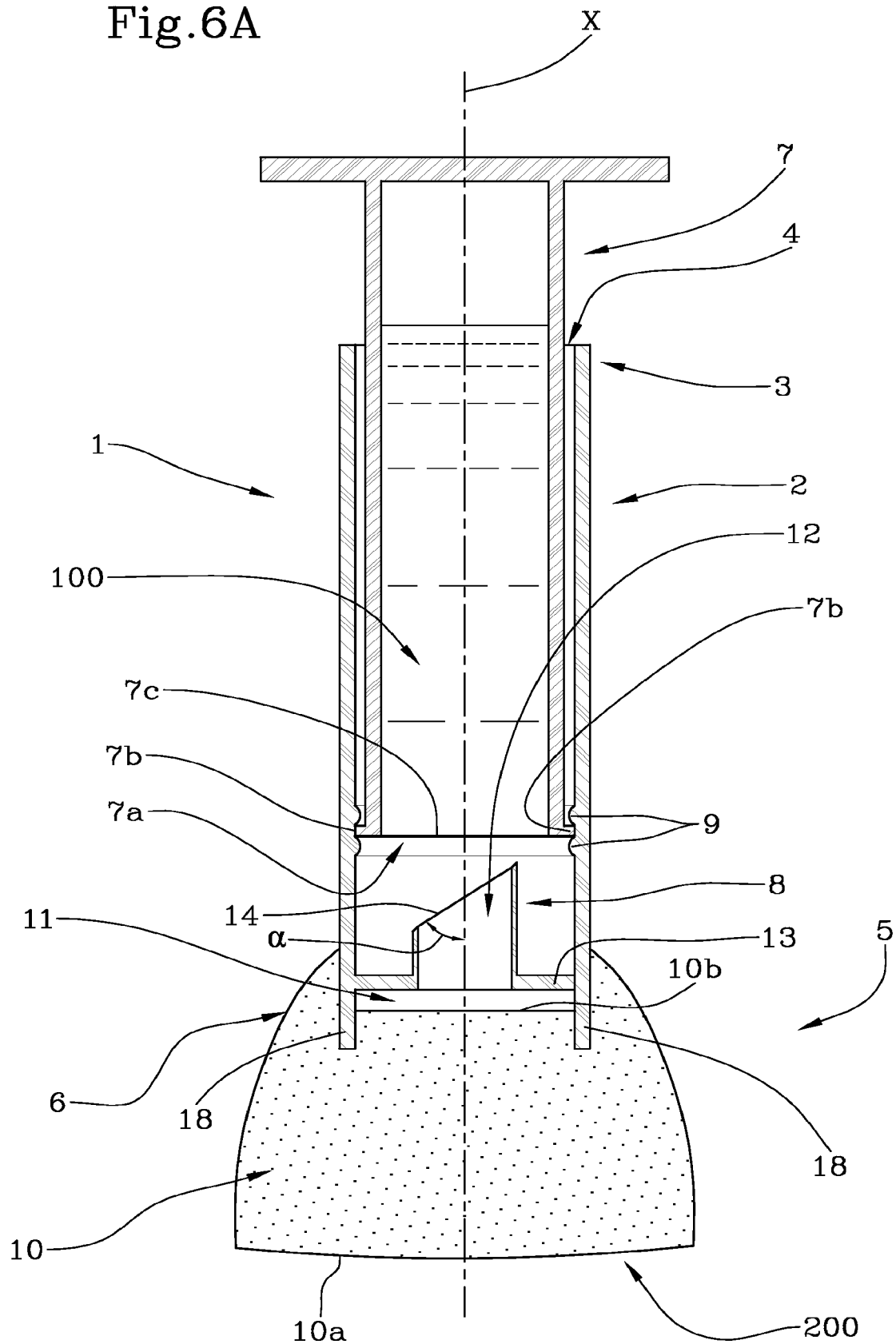
FIGS. 6a and 6b each represent a sectional side view of the device for the application of liquid medical substances to which the present invention relates according to a third embodiment, in a non-operational and operational condition, respectively.
Figure 6B:
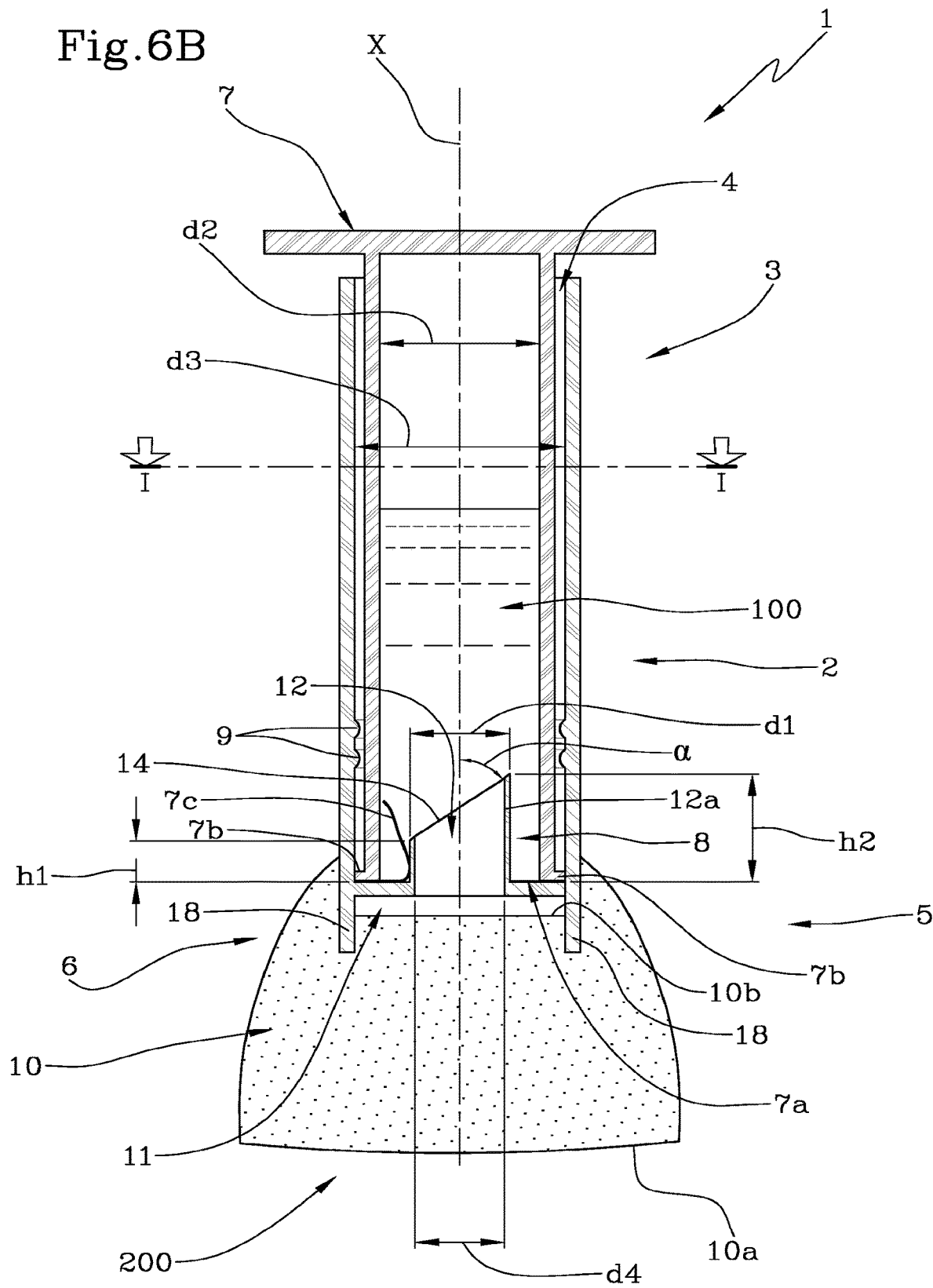

A third embodiment, not illustrated, envisages that the two base surfaces 10a and 10b are parallel to each other but both inclined relative to the axis X as a result of the inclination of the flanged base 15 relative to the axis X. FIGS. 6A and 6B represent a further embodiment the delivery portion 5 is defined by the same extension 18 of the side walls of the housing portion 3, but unlike in the configuration illustrated in FIGS. 5A and 5B, the two extensions do not surround the pad 10 but are rather embedded within it.

In detail, the extension 18 of the side walls of the main body 2 is coated with glue, rested upon the base surface 10b of a pad 10 originally having a cylindrical shape with the base walls 10a and 10b parallel to each other and then pushed inside the pad 10. This pressure causes the base surface 10b to collapse, draws the side walls of the pad 10 toward the exterior walls of the main body 2 and causes it to take on the shape illustrated in FIGS. 6A and 6B. The free base surface 10a becomes slightly curved, taking on a convex shape.

This configuration is advantageous for several reasons; in fact, given the absence of the flanged base 15, a smaller quantity of plastic material is required, there is no portion of plastic that can come into contact with the skin since it is the pad that surrounds the main body and not vice-versa, and, moreover, there is a larger exposed surface of the pad available for applying the liquid, as not only the base surface 10a but also the side walls of the pad can be easily used.

Advantageously, the delivery portion 5 also has an air chamber 11 interposed between the perforating element 8 and the pad 10.

The air chamber 11 has a smaller diameter than the pad 10, preferably equal to the size of the inner diameter $d_3$ of the housing portion 3 of the cylindrical body 2, and a height or depth preferably equal to or less than the inner diameter $d_4$ of the cylindrical conduit 12 of the perforating element 8. Advantageously, the height of the air chamber 11 is equal to at least one third of the inner diameter $d_4$, preferably equal to half of the diameter $d_4$.

The air chamber permits part of the liquid to be accumulated in order to better impregnate the pad and enable good drainage and an effective delivery of the liquid. In order to render the drainage of the medical substance on the pad more rapid and immediate, based on the physicochemical characteristics of the medical substance applied, the air chamber can be expanded through an additional volume of air obtained inside the pad 10, in particular by means of a cavity, not illustrated, fashioned in the base surface 10b, and adjacent to the air chamber 11.

In order to better understand the geometric and dimensional relationships of these elements, the features of the cylindrical conduit 12 will be described in detail below.

With reference to the reservoir 7, it has a cylindrical shape, with a cross section equal to that of the housing portion 3, and is preferably circular for the whole of its extent in order to be inserted inside the latter.

The preferred conformation, illustrated in the appended figures, shows the reservoir having a cylindrical shape with a circular cross section and an inner diameter d2 comprised between 10 and 20 mm Preferably, the reservoir 7 has the aforesaid openable end 7a as wide as the inner diameter d2 of the reservoir 7 and sealed by a protective film so as to preserve the liquid 100 by isolating it from the outside environment 200.

Preferably, said film can be glued or heat-welded along the flange-shaped edge 7b, and consists of a plastic polymer (by way of example: PE, PP, HDPE, LDPP) or a plastic polymer film bonded with a metal film, preferably aluminium.

Preferably, according to the preferred embodiment, the cartridge reservoir 7 has an internal capacity in terms of volume comprised between 1 and 100 ml, preferably between 2 and 50 ml.

Other capacity values of the reservoir 7 and hence of the outer dimensions thereof, as well as the inner diameter d2, can in any case be envisaged within the technical field of use of the present invention, giving rise to further and different embodiments, not illustrated in the appended figures, of the device 1.

Preferably, on the end that remains outside the housing body 3, and thus opposite the openable end 7a, the reservoir 7 can have an annular edge such as to create a supporting base capable of keeping the device 1 in an upright position, for example both during storage and in an operational condition of use of the same. An upright position means that the axis X is disposed vertically, the pad 10 of the device 1 is turned upward and the supporting base of the reservoir 7 is in contact with a flat surface.

The slant of the cylindrical conduit 12 which derives from the cutting edge 14 defines two distinct values of the height of the wall 12a relative to the base 13—a lesser h1 and a greater h2—when measured in the direction of the longitudinal axis X.

Preferably, the greater value of the second height h2 of the wall 12a is equal to at least al 70% of the inner diameter d4 of the cylindrical conduit 12. Preferably, the lesser value of the first height h1 of the wall 12a is equal to at least 50% of the inner diameter d4 of the cylindrical conduit 12. In this manner, the border of the openable end 7a, which is torn and remains inside the reservoir 7 constrained to the flange-shaped edge 7b, will not risk obstructing the cylindrical conduit 12 when the device is in use. Other inclinations of the cutting edge 14 can give rise to different wall shapes and heights, variants which are not illustrated in the appended figures but fall within the scope of the same functional concept. Advantageously, as has been noted, the cylindrical conduit 12 of the perforating element 8 enables the housing portion 3 to be placed in fluid communication 100 with the delivery portion 5.

Advantageously, in greater detail, the cylindrical conduit 12 of the perforating element 8 enables the internal volume of the reservoir 7 to be placed in fluid communication 100 with the pad 8 after the sealing cap placed on the openable end 7a of the reservoir 7 has been broken.

In fact, the perforating element 8, in this case the cutting edge 14 thus configured, provides a slant that enables the film present on the openable end 7a to be perforated and torn open progressively and gradually in a much faster and precise manner.

As can be seen in the appended figures, the outer diameter d1 of the cylindrical conduit 12 is such as to be smaller than the inner diameter d2 of the reservoir 7; in this manner the penetration of the cutting edge 14 through the openable end 7a, sealed by the protective film described above, can be carried out perfectly.

The outer diameter d1 of the perforating element 8 is preferably comprised between 50% and 80%, more preferably between 60% and 70%, of the inner diameter d2 of the reservoir 7. In this manner, the ratio between the diameters and the liquid drainage space enable an outflow with a calibrated dosage.

In one embodiment in which the volume of the reservoir is 12 ml and the diameter of the cylindrical conduit 12 is equal to 8 mm, a substantially complete outflow is obtained in a period of time of between 2 and 5 seconds, preferably about 3 seconds.

Advantageously, in this time of outflow of the liquid 100, the pad 10 has immediately been impregnated with the pre-established optimal quantity, unlike what can be found in the prior art.

In detail, the operation of the device 1, in an operational condition of use—in particular of activation of the device 1—requires health personnel to press the cartridge reservoir 7 (already preloaded in the device and held in position by means of the reversible locking described above) from the pre-established rest position all the way down into the activation position with one hand, while gripping the device 1 by means of the main body 2 with the other hand.

In other words, the manual action of health personnel moves the reservoir 7 from the reversible locking position into the activation position, until the shaped edge 7b comes up against the base 13 of the perforating element 8.

It is evident that the operation of activating the device 1 with the methods described above is simple, delivery is fast and the application takes place under complete asepsis unlike in the prior art: in fact, the cutting edge 14 tears open the film of the openable end 7a of the reservoir 7a in a clean and precise manner.

Advantageously, the cylindrical conduit 12 of the perforating element 8 is of a form that does not obstruct the outflow of the liquid, but rather promotes it and conveys it directly toward the pad 10 without any dispersion at the sides. Advantageously, in greater detail, the shape of the cutting edge 14 is such as to move the cut film border without creating any loose fragments of the same, which could for example obstruct the outflow of the medical liquid 100 through the cylindrical conduit 12.

In fact, once the device 1 has been activated by health personnel, the only passage of the liquid 100 between the housing portion 3 and the delivery portion 5, or even better, between the reservoir 7 and the pad 10, takes place exclusively by means of the cylindrical conduit 12.

Advantageously, in the device 1 when activated, the position of the shaped edge 7b together with the base 13 of the perforating element 8 ensures a hermetical seal for the medical liquid 100.

In this state of the device 1, involuntary leaks or dispersions of the medical liquid 100 no longer occur, as is probable, in contrast, according to the prior art.

Advantageously, with the hermetic seal formed between the shaped edge 7b and the annular base 13, the device 1 can be easily used by health personnel in any preferred position: vertical, with the pad 10 turned up or with the pad 10 turned down, or else in a horizontal position or in any intermediate position between them.

The perforating element 8 can be configured so as to accommodate within it a colouring substance that reacts chemically with the medical liquid 100 only at the moment of activation of the device 1: in this manner the medical liquid 100 will be clearly evident during the application thereof, preventing health personnel from leaving portions of the patient's skin untreated. The substance is closed inside the cylindrical conduit 12 by a membrane that is soluble on contact with the medical liquid or can be impregnated in a pad situated inside the air chamber 11 or in the cylindrical conduit 12 or dispersed in the cavity of the pad.

A further distinctive feature of the device 1 is the fact that the cylindrical conduit 12 is the only element that regulates the outflow of the medical liquid 100 during the activation of the device 1 and subsequently during the application of the liquid 100 on the patient's skin.

Advantageously, the variation, on each occasion, of the inner diameter d4 of the cylindrical conduit 12 according to the different configurations of the perforating element 8, enables an outflow at a calibrated dosage in terms of flow rate (i.e. ml/sec), based on each type of medical liquid 100 delivered into the pad 10.

Advantageously, with this outflow rate of the liquid 100 the pad 10 is evenly impregnated with the optimal pre-established quantity, unlike what may be found in the prior art.

Advantageously, the air chamber 11 present between the pad 10 and the perforating element 8 is such as to favour and considerably improve the system of channelling the medical liquid 100, contributing to the rapid discharge of the liquid without there being any need for further operations on the part of health personnel during use, for example patting or dabbing the material of the pad 10 in order to activate and/or speed up the impregnation thereof.

Advantageously, other medical liquids can be used with the present device 1, by suitably calibrating the inner diameter d1 of the cylindrical conduit 12. It is evident that the inner diameter d1 of the cylindrical conduit 12 is an important calibration parameter, in terms of both time (seconds) and flow rate (ml/s), for optimal delivery of the medical liquid 100 achieved by means of the device 1 of the present invention.

Advantageously, the calibration of the inner diameter d4 makes it possible to obtain a better outflow of the liquid 100 and better application of the same in terms of time and flow rate.

This result is achieved by the device 1 independently of the characteristics of the medical liquid 100 used, whether they are alcohol based or contain surfactants; preferably, to ensure a better and further effectiveness of the device 1, the medical liquid 100 should have a surface tension of less than 72.80 mN/m and preferably around 23 mN/m.

Advantageously, the perforating element 8 can be made in one piece with the main body 2 or else it can be made separately and inserted into the main body 2 during assembly with a pre-established interference that ensures a hermetic seal of the coupling between the element 8 and interior walls of the body 2.

This aspect makes it possible, advantageously, to have the perforating body 8 made of a different material than the other elements of the device 1 (for example the body 2 and the reservoir 7); by way of example, it can be made of a plastic or metallic material, or can have portions made of different materials.

It is evident that the combination of different sizes of the outer diameter d1 of the cylindrical conduit 12 and of the cutting edge 14 of the perforating element 8, as well as of the inner diameter d2 of the reservoir 7 and obviously the inner diameter d3 of the main body 2 which houses both elements (reservoir 7 and perforating element 8), produces different configurations of the aforesaid elements and also different embodiments of the entire device 1.

Only one possible preferred, but not exclusive, embodiment of the device 1, was illustrated deliberately.

Advantageously, all of the elements making up the device 1 can be made with materials compatible with the traditional sterilization techniques used in the medical realm (by way of example: a gas with ethylene oxide, or with "Beta" or "Gamma" rays).

Preferably, the device 1 can be made completely of, or one of its main elements can be made of a plastic material such as PP, PE or HDPE or other non-plastic materials.

In this regard, advantageously, the device 1 is capable of ensuring maximum levels of asepsis by means of a protective film applied preferably at the end of the process of production of the device 1; preferably the covering is a heat-shrinkable film that completely envelops the device 1.

The peculiarity of the numerous angular variants in the position of the pad 10 relative to the axis X of the main body 2 permits a better, more effective use of the device 1 itself, maximizing the distribution of the medical liquid 100 on the patient's skin without leaks or involuntary dripping, which may sometimes be dangerous.

The hollow structure of the perforating element 8 of the device 1 described no longer consists of a central perforating tip with peripheral outflow channels as in the prior art, but is rather an element of control and dosage assuring that the outflow itself is calibrated based on a quantity that is pre-established on each occasion.

Advantageously, overall the device 1 enables a more rapid, effective and precise use, facilitating the work of personnel assigned to provide emergency aid, where time and effectiveness of action are of fundamental importance.

The invention claimed is:

1. A device for the application of liquid medical substances, comprising:
    a main body comprising a housing portion and a delivery portion;
    a cartridge reservoir suitable for being inserted into said housing portion;
    a perforating element disposed inside said main body;
    wherein said perforating element has at least one cutting edge which serves to place said housing portion in fluid communication with said delivery portion, and
    wherein said perforating element has a base for connecting with said main body and has a first height not less than 50% of an inner diameter of the perforating element and a second height, not less than 70% of the inner diameter of the perforating element,
    and wherein said first height is defined as a height between the lowest point of said at least one cutting edge and said base and said second height is defined as a height between the highest point of said at least one cutting edge and said base.

2. The device according to claim 1, wherein said delivery portion further comprises a pad configured to deliver a liquid to a patient's skin.

3. The device according to claim 1, wherein the housing portion further comprises a retaining means configured to interact with said cartridge reservoir for keeping said cartridge reservoir stably in a position of partial insertion.

4. The device according to claim 1, wherein said cartridge reservoir is configured to move in an axial direction to place said housing portion in fluid communication with said delivery portion.

5. The device according to claim 4, wherein said cartridge reservoir contains a liquid medical substance therein and wherein axial movement of the cartridge reservoir causes release of the medical substance therein to the delivery portion.

* * * * *